(12) United States Patent
Levin et al.

(10) Patent No.: US 6,984,761 B2
(45) Date of Patent: Jan. 10, 2006

(54) CO-PRODUCTION OF PHENOL, ACETONE, α-METHYLSTYRENE AND PROPYLENE OXIDE, AND CATALYST THEREFOR

(75) Inventors: Doron Levin, Annandale, NJ (US); C. Morris Smith, West University Place, TX (US); Jose Guadalupe Santiesteban, Baton Rouge, LA (US); James C. Vartuli, Schwenksville, PA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 10/320,237

(22) Filed: Dec. 16, 2002

(65) Prior Publication Data

US 2004/0116749 A1 Jun. 17, 2004

(51) Int. Cl.
C07C 45/33 (2006.01)
C07C 37/68 (2006.01)
C07C 37/08 (2006.01)
C07C 4/02 (2006.01)

(52) U.S. Cl. .................. 568/385; 568/386; 568/396; 568/397; 568/411; 568/749; 568/754; 568/798; 585/440

(58) Field of Classification Search ............... 568/385, 568/386, 396, 397, 411, 749, 754, 798; 585/440; 502/102
See application file for complete search history.

(56) References Cited

U.S. PATENT DOCUMENTS

| | | | |
|---|---|---|---|
| 2,757,209 A | 7/1956 | Joris | 260/621 |
| 2,854,487 A | 9/1958 | Quin | 260/618 |
| 3,403,193 A | 9/1968 | Russell | 260/669 |
| 4,358,618 A | 11/1982 | Sifniades et al. | 568/385 |
| 4,853,197 A * | 8/1989 | Wilson et al. | 423/306 |
| 5,015,786 A | 5/1991 | Araki et al. | 568/798 |
| 5,245,090 A | 9/1993 | DeCaria et al. | 568/798 |
| 5,371,305 A | 12/1994 | Hood | 568/798 |
| 5,463,136 A | 10/1995 | Blackbourn et al. | 568/385 |
| 5,905,178 A * | 5/1999 | Hildreth | 585/258 |
| 5,932,751 A | 8/1999 | Carroll et al. | 549/529 |
| 5,998,677 A | 12/1999 | Yasaka et al. | 568/798 |
| 6,114,551 A | 9/2000 | Levin et al. | 549/510 |
| 6,169,215 B1 | 1/2001 | Levin et al. | 568/798 |
| 6,169,216 B1 | 1/2001 | Levin et al. | 568/798 |
| 6,297,406 B1 | 10/2001 | Levin et al. | 568/798 |
| 6,410,804 B1 | 6/2002 | Levin et al. | 568/798 |

FOREIGN PATENT DOCUMENTS

| | | |
|---|---|---|
| GB | 1 133 313 | 11/1968 |
| JP | 56-140935 | 11/2004 |
| WO | WO98/27030 | 6/1998 |
| WO | WO99/42426 | 8/1999 |

OTHER PUBLICATIONS

Grzegorz Lewandowski and Eugeniusz Milchert: Integrated Production of Propylene Oxide, Phenol and Acetone, Institute of Organic Chemical Technology in Szczecin, Przemyst Chemiczny 79, No. 12, pp. 410-411 (2000).

Abstract, SU 462,812, V.A. Levshtein, "Phenol, acetone, alpha-methylstyrene simultaneous production—by decomposition of cumene hydroperoxide and 2-phenyl propan -2-01 mixture in presence of an acidic catalyst", Aug. 18, 1975.

* cited by examiner

Primary Examiner—Johann Richter
Assistant Examiner—Sikarl A. Witherspoon
(74) Attorney, Agent, or Firm—Darryl M. Tyus

(57) ABSTRACT

A process is disclosed for producing α-methylstyrene, acetone, and phenol wherein the amount of α-methylstyrene produced may be controlled by selectively converting a portion of the cumene hydroperoxide to dimethyl phenyl carbinol, the hydrated form of α-methylstyrene. The dimethyl phenyl carbinol thus produced will lead to increased production of α-methylstyrene upon dehydration in the acid cleavage unit of the phenol plant. By controlling the fraction of the cumene hydroperoxide reduced to dimethyl phenyl carbinol, the amount of α-methylstyrene produced in the plant can be continuously set to meet the demand of the market for α-methylstyrene. Also disclosed is a non-acidic catalyst for reduction of cumene hydroperoxide.

39 Claims, 2 Drawing Sheets

CO-PRODUCTION OF PHENOL, ACETONE, α-METHYLSTYRENE AND PROPYLENE OXIDE, AND CATALYST THEREFOR

FIELD OF THE INVENTION

This invention relates to the co-production of phenol, acetone, α-methylstyrene and optionally, propylene oxide, and catalyst therefor; more particularly to a process and catalyst for producing phenol, acetone and α-methylstyrene from cumene hydroperoxide.

BACKGROUND OF THE INVENTION

Increased amounts of α-methylstyrene (AMS) may be produced in a combined phenol and acetone plant by selectively reducing cumene hydroperoxide (CHP) to dimethyl phenyl carbinol (DMPC), the hydrated form of AMS. DMPC is also known as 2-phenyl-2-propanol or dimethylbenzyl alcohol (DMBA). As a byproduct of the oxidation of cumene to CHP, small amounts of DMPC are produced. The DMPC undergoes dehydration in the presence of an acid catalyst to yield AMS. Some phenol manufacturers recover the AMS if it is produced in sufficient quantities. Other phenol manufacturers do not recover AMS, but hydrogenate it back to cumene for recycle to the oxidation reactor. The hydrogenation of the AMS may take place after recovery of an AMS/cumene stream in the distillation section of the phenol plant. As an alternative approach, the entire cleavage reactor effluent, including all of the AMS may be hydrogenated prior to separation of the phenol and acetone in the distillation section of the plant, e.g., U.S. Pat. No. 5,245,090.

AMS is used industrially in a variety of applications, particularly in the production of certain copolymers and specialty polymers. In addition, AMS finds utility as an intermediate in the production of fine chemicals such as unsaturated AMS dimers. These dimers are used as molecular weight controlling agents in the production of copolymers, such as acrylonitrile-butadiene-styrene resins and styrene-butadiene rubber. The hydrogenated forms of AMS dimers are of industrial value as components in lubrication compositions.

A number of patented processes have been developed in an attempt to increase the AMS yield in the production of phenol from cumene. These processes typically seek to increase the AMS yield by minimizing the loss of AMS through secondary reactions. One approach employs a multi-step process that reacts CHP and DMPC with sulfuric acid in a back mixing reactor to produce dicumyl peroxide that subsequently undergoes decomposition at elevated temperature under plug-flow conditions to produce AMS, phenol, and acetone e.g., U.S. Pat. No. 4,358,618. An alternative approach to minimize the loss of AMS through secondary reactions employs a multi-step process that decomposes the CHP in a back mixing reactor followed by dehydration of the DMPC in a plug-flow reactor after an inhibitor such as acetone and/or water has been added to control secondary reactions of AMS, e.g., U.S. Pat. Nos. 5,998,677 and 5,463, 136. These processes, however, do not increase the yield of AMS over the theoretical maximum that can be obtained by full dehydration of the DMPC produced in the oxidizer unit. These processes merely seek to minimize the loss of AMS to heavy byproducts, and result in AMS yields of 70–80% of the theoretical maximum based on the DMPC exiting the oxidizer unit.

The process of this invention provides a method for increasing the AMS yield above the theoretical maximum based on the DMPC in the oxidizer effluent by reducing a portion of the CHP stream to DMPC over a suitable heterogeneous catalyst. This process stream, having elevated amounts of DMPC, can then be fed to the cleavage unit of a phenol plant where the remaining CHP undergoes acid-catalyzed decomposition to phenol and acetone. During the decomposition, the acid catalyst dehydrates the DMPC to AMS. By controlling the fraction of the CHP reduced to DMPC, the amount of AMS produced in the plant can be continuously set to meet the demand of the market.

The process of this invention also provides a method for controlling the AMS yield by reacting a portion of the CHP with an exogenous source of propylene in an epoxidation reaction. In the epoxidation reactor, a portion of the CHP is reduced in the presence of an epoxidation catalyst to DMPC with propylene going to propylene oxide. The propylene oxide can be recovered as a valuable byproduct. The liquid solution leaving the epoxidation reactor has elevated amounts of DMPC, and can then be fed to the cleavage unit of a phenol plant where the remaining CHP undergoes acid-catalyzed decomposition to phenol and acetone. During the decomposition, the acid catalyst can dehydrate DMPC to AMS. By controlling the fraction of the CHP reduced to DMPC, the amount of AMS produced in the plant can be continuously set to meet the demand of the market for AMS.

No process currently exists that allows a phenol manufacturer to make on-demand AMS. AMS may only be recovered from dehydration of DMPC produced in the oxidation reactor. Current processes do not allow flexibility in controlling the amount of DMPC produced via oxidation as unfavorable side reactions lead to higher quantities of acetophenone when DMPC levels are increased by oxidation. Numerous methods have been disclosed in the patent literature to maximize the yield of AMS, regardless of whether AMS is recovered as a separate product or hydrogenated to cumene and recycled. These methods for improving the AMS yield seek to minimize side reactions of the AMS by using acetone as a solvent to dilute the AMS or using alternative reactor configurations. Regardless of the method used, the maximum AMS yield for current state-of-the-art plants is typically within the range of 70–80% based on the DMPC leaving the oxidation reactor.

SUMMARY OF THE INVENTION

This invention includes a process for co-producing AMS along with acetone and phenol which comprises the steps of oxidizing a stream containing cumene in the presence of an oxygen-containing stream to form a stream containing CHP. A portion of the CHP stream may be reduced in the presence of a catalyst, preferably a non-acidic catalyst to form a stream containing DMPC. The DMPC-containing stream and the remaining portion of said CHP stream are converted in the presence of a catalyst, preferably an acidic catalyst to form a product stream containing AMS, acetone, and phenol. AMS, acetone, and phenol are each separated from said product stream. In this invention, the amount of CHP reduced to DMPC may be varied from about zero up to about 50 weight percent of the stream containing CHP.

This invention also includes a process for co-producing AMS and propylene oxide along with acetone and phenol which comprises the steps of oxidizing a stream containing cumene in the presence of an oxygen-containing stream to form a stream containing CHP. A portion of the CHP stream may be reduced in the presence of an epoxidation catalyst and a propylene-containing stream to form a stream containing DMPC and propylene oxide. Propylene oxide is separated from the reaction stream leaving a stream containing DMPC. The DMPC-containing stream and the remaining portion of said CHP stream are converted in the presence of a catalyst, preferably an acidic catalyst, to form a product stream containing AMS, acetone, and phenol. AMS, acetone, and phenol are each separated from said product stream. In this invention, the amount of CHP reduced to DMPC may be varied from about zero up to about 50 weight percent of the stream containing CHP.

This invention further includes a non-acidic catalyst for reduction of cumene hydroperoxide to dimethyl phenyl carbinol, said catalyst contains a metal and a catalyst support, preferably cobalt supported on zirconium oxide or on aluminophosphates.

DETAILED DESCRIPTION OF PREFERRED EMBODIMENTS

Figure 1:
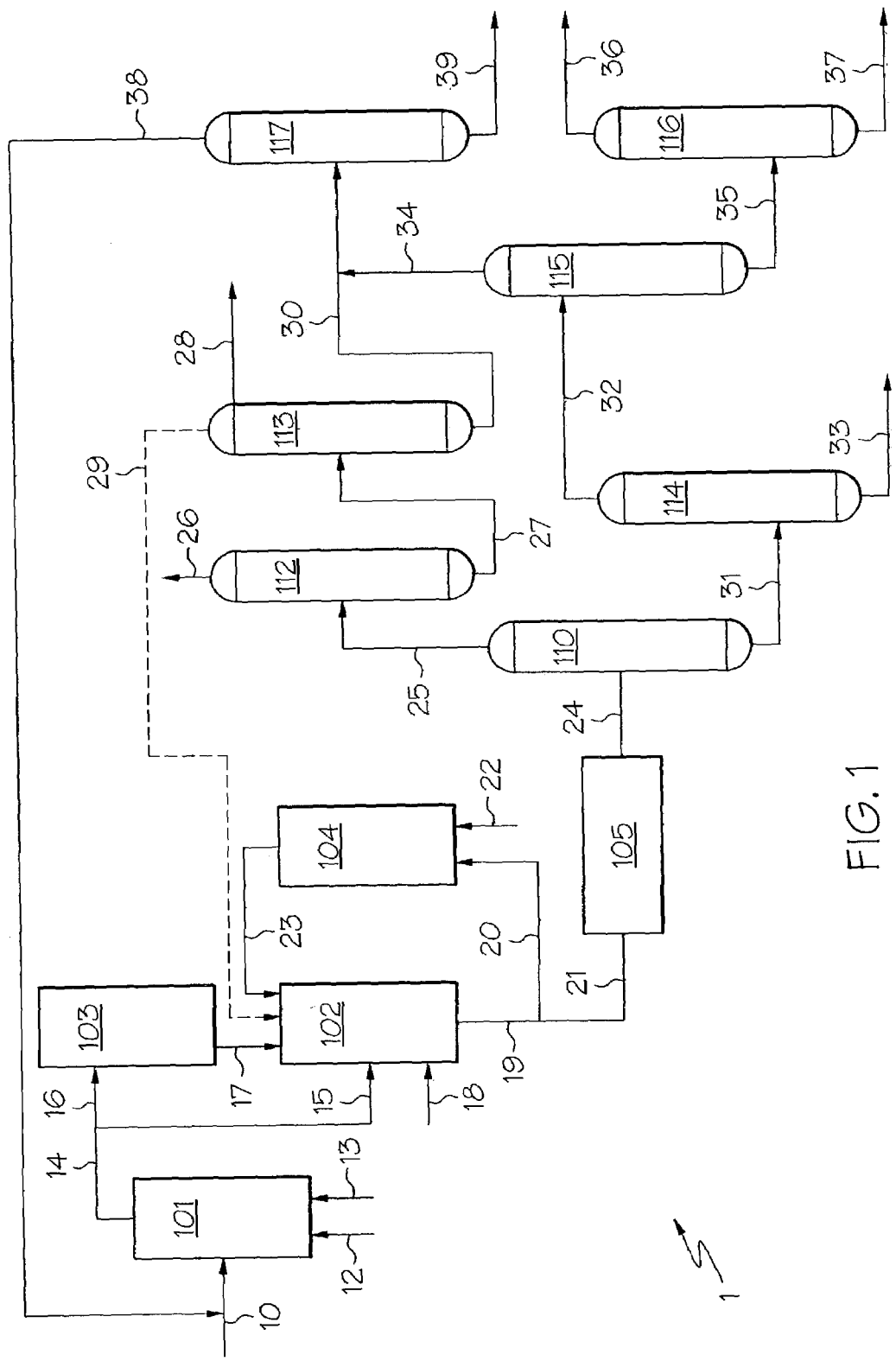
FIG. 1 is a schematic flow diagram of a processing scheme for the co-production of phenol, acetone, and AMS.

FIG. 1 represents a schematic flow diagram of an embodiment of this invention as processing scheme 1 for the co-production of phenol, acetone, and AMS. Cumene in stream 10 is fed to an oxidation reactor 101 where CHP is produced by reaction of the cumene with oxygen from the air fed as stream 12. Initiators to facilitate the oxidation of the cumene may be added as stream 13. Preferably, these initiators may be an organic hydroperoxide, such as CHP, tert-butyl hydroperoxide, ethylbenzene hydroperoxide or the like. Alternatively, these initiators may be azo type free radical initiators or peroxy type free radical initiators that are known to catalyze the oxidation of organic hydrocarbons. Examples of such azo type free radical initiators and peroxy type free radical initiators that may be used in the process of the invention are described in Encyclopedia of Polymer Science and Engineering, Volume 2, Page 143 et seq., 1985, and Volume 11, Page 1 et seq., 1988, respectively. The CHP stream 14, containing DMPC and acetophenone, together with unreacted cumene may be concentrated by removing a portion of the unreacted cumene prior to the cleavage section of processing scheme 1 (not shown).

In an embodiment of this invention where increased amounts of AMS are produced together with phenol and acetone, the CHP stream 14 is then split into streams 15 and 16, with the split ratio α=16/15 set according to desired plant output of AMS. Stream 16 is fed to the reduction reactor 103 where a portion of the CHP in stream 16 is reduced to DMPC over a suitable catalyst. Stream 17 leaving the reduction reactor has an increased concentration of DMPC relative to CHP stream 14. Preferably, in order to minimize the conversion of CHP to phenol and acetone in reduction reactor 103, the catalyst used therein may be a heterogeneous catalyst comprised of a non-acidic or low acidity catalyst support and a metal. Non-acidic or low acidity catalyst supports include, but are not limited to, silica, alumina, crystalline or amorphous aluminophosphates; Group 4 metal oxides, such as titania, zirconia, hafnia, and mixtures thereof; and mesoporous molecular sieves exemplified by MCM-41. The metal deposited on such catalyst supports includes, but is not limited to, a Group 8, Group 9, or Group 10 transition metal, such as cobalt, iron, nickel, or mixtures thereof; a Group 2 metal, such as magnesium, calcium, barium, or mixtures thereof; a Group 1 metal, such as lithium, sodium, cesium, and mixtures thereof; a Group 3 metal, such as scandium, yttrium, lanthanum, or mixtures thereof; or mixtures and/or combinations of the above. Group numbers used in this patent application are from the Periodic Table of the Elements using the IUPAC format described in the *CRC Handbook Chemistry and Physics*, 79th Edition, CRC Press, Boca Raton, Fla. (1998).

More preferably, such heterogeneous catalysts may be a Group 8, Group 9 or Group 10 transition metal on a support, such as cobalt supported on a Group 4 metal oxide, such as zirconium oxide, or cobalt supported on aluminophosphate, as disclosed in Examples 1 and 3, discussed below. These mixed metal oxides can be prepared by typical methods known to those skilled in the art such as impregnation, incipient wetness or ion exchange, or they can be prepared by co-precipitation of the metal oxides from soluble salt solutions.

Streams 15 and 17 are fed to first cleavage reactor 102 where an acidic catalyst decomposes the CHP into phenol and acetone, and dehydrates the DMPC into AMS. The acidic catalyst may be in the liquid phase, such as sulfuric acid, fed via stream 18. Preferably, the catalyst may be in the solid phase, such as a solid acid catalyst, capable of decomposing hydroperoxides into alcohols and ketones. Such solid acid catalysts include catalysts produced by calcining a source of a Group 4 metal oxide with a source of an oxyanion of a Group 6 metal at a temperature of at least 400° C., as disclosed in U.S. Pat. No. 6,169,215; sulfated transition metal oxides, as disclosed in U.S. Pat. No. 6,169,216; and a mixed metal oxide of cerium and a Group 4 metal, as disclosed in U.S. Pat. No. 6,297,406. The disclosures of U.S. Pat. Nos. 6,169,215; 6,169,216; and 6,297,406; are fully incorporated herein by reference. The effluent from first cleavage reactor 102, stream 19, is composed of phenol, acetone, AMS, acetophenone, cumene, and some heavies produced from secondary reactions.

To minimize the formation of heavies in any of the embodiments described herein, it is preferable to dilute the AMS in the cleavage reactor. One possible diluting stream is the product itself. If first cleavage reactor 102 is operated with a solid acid catalyst, such as those described in U.S. Pat. Nos. 6,169,215; 6,169,216; and 6,297,406, in a plug flow reactor configuration, it is desirable to have as low as possible an AMS concentration at the inlet to minimize secondary reactions of the AMS. To achieve this goal, it is desirable to minimize the AMS in the diluting stream 23. This may be achieved by hydrogenating a portion of the effluent stream 19 as stream 20. Stream 20 is hydrogenated in hydrogenation reactor 104 in the presence of hydrogen stream 22 and a hydrogenation catalyst (not shown).

Preferably, the hydrogenation catalyst for use in the hydrogenation reactor 104 includes a hydrogenation component and a catalyst support. The hydrogenation component of the hydrogenation catalyst may be derived from a Group 8, Group 9, or Group 10 transition metal, such as platinum, iridium, osmium, palladium, rhodium, ruthenium, nickel, cobalt, iron, and mixtures of two or more thereof. Preferred metals are palladium and platinum. A Group 8, Group 9 or Group 10 transition metal may optionally be mixed with a Group 14 metals, preferably tin, and/or a Group 7 metal, preferably rhenium and manganese. Other metals known in the art capable of acting as a hydrogenation component include, but are not limited to, a Group 6 metal, such as tungsten, and molybdenum; a Group 11 metal, such as copper, silver, and gold, either alone, or in combination.

The amount of the hydrogenation component may be in the range of 0.001 to 30 wt.% of the total catalyst, preferably from 0.01 to 5 wt.%. The hydrogenation component can be exchanged onto the support material, impregnated into it or physically admixed with it. Suitable catalyst support materials are those well known in the art, for example, alumina, silica, clay, carbon, zirconia, titania, and mesoporous molecular sieves, as exemplified by MCM-41 type materials and mixtures thereof.

The diluting stream 23 may be fed completely into the front end of first cleavage reactor 102. Alternatively, the diluting stream 23 may be fed in one or more stages down the length of the bed to provide the necessary diluting effect. The split ratio $\beta=20/21$ is set to provide the necessary diluent to minimize the formation of heavy components. Increasing $\beta$ reduces the amount of heavy components produced in the cleavage reactor(s), but does so at the cost of a loss of recoverable AMS. In addition to providing the necessary dilution to the cleavage reactor, stream 23 may be cooled prior to entering first cleavage reactor 102 to assist in heat removal from the reactor. As an alternative diluent, or in addition to the product recycle, acetone from the acetone tower 113 may be returned to the cleavage reactor in stream 29.

Stream 21 from the first cleavage reactor 102 may be sent to a second cleavage reactor 105. Second cleavage reactor 105 may be operated at conditions that are the same or are different than those in first cleavage reactor 102. For example, second cleavage reactor 105 may be operated at a higher temperature than first cleavage reactor 102. Second cleavage reactor 105 would typically be a plug-flow reactor, and may, or may not contain a catalyst bed. If a liquid acid such as sulfuric acid is used in first cleavage reactor 102, there may be sufficient acidity remaining in stream 21 to catalyze the necessary reactions in second cleavage reactor 105. In a preferred embodiment, second cleavage reactor 105 contains a solid acidic catalyst, such as those described in U.S. Pat. Nos. 6,169,215; 6,169,216; and 6,297,406. Second cleavage reactor 105 is used to decompose any dicumyl peroxide that may form in first cleavage reactor 102, and convert any residual CHP to phenol and acetone. In an alternative embodiment, a series of two or more reactors may be used for final conversion of the CHP, and a diluent such as acetone may or may not be added before each reactor bed.

In an alternate embodiment of this invention, processing scheme 1 may be operated to produce phenol and acetone with minimal amounts of AMS produced. When operating in this mode, the split ratio $\alpha$ is zero wherein all of CHP stream 14 is fed to first cleavage reactor 102 (as stream 15), thereby bypassing reduction reactor 103. Diluent stream 23, and optionally stream 29, along with stream 15 are then fed to first cleavage reactor 102 in the presence of an acidic catalyst wherein CHP is decomposed to phenol and acetone. Such acidic catalyst is preferably a solid acid catalyst that is capable of decomposing hydroperoxides, such as those disclosed above. Effluent stream 19 in this embodiment is comprised mainly of phenol, acetone, cumene, and small amounts of AMS and heavies. Diluent stream 23 is formed by hydrogenating stream 20, a portion of effluent stream 19, in hydrogenation reactor 104 using a suitable hydrogenation catalyst, such as those disclosed above. Stream 21, the remaining portion of effluent stream 19, may then be fed to a secondary cleavage reactor 105 for further conversion, if desired.

In still another embodiment of this invention, a two-bed, single reactor may be used (not shown) for reduction and cleavage since the reaction temperatures for DMPC formation and CHP cleavage are similar. A top bed may contain a heterogeneous catalyst that does not convert significant amounts of CHP to phenol and acetone, as discussed above, to produce DMPC to give the desired AMS yield. The bottom bed may contain a suitable acidic catalyst to decompose the remaining CHP to phenol and acetone and dehydrate the DMPC to AMS.

While it is preferable to use a solid catalyst in cleavage reactors 102 and 105, as discussed above, it is within the scope of this invention to utilize liquid acids, such as sulfuric acid, to accomplish the decomposition of the CHP (not shown). If use is made of liquid acids, a neutralization step would be required prior to the recovery section of the plant. Such a neutralization step may employ liquid bases or ion exchange resins or the like, as is well known to those skilled in the art.

There are many ways known to those skilled in the art to separate the individual components from stream 24 exiting the cleavage section of the plant. The following distillation scheme is presented for illustrative purposes only. Stream 24 from cleavage reactor 105 is sent to the Crude Acetone Tower 110 where acetone and the lighter components are separated from phenol and the heavier components. The overhead stream 25 is sent to the Lights Topping Tower 112 where light compounds such as acetaldehyde are removed as stream 26. The bottoms from the topping tower, stream 27 are fed to the Refined Acetone Column 113, where product specification acetone is recovered as stream 28. The bottoms from the Crude Acetone Tower 110, stream 31, comprising phenol, and some AMS, cumene, acetophenone and heavies, are fed to the Heavy Ends Tower 114, where the heavy components are separated as stream 33. The overhead stream 32 is fed to the Hydrocarbon Removal Tower 115, where the residual AMS and cumene are separated from the phenol and pass to the AMS recovery section as stream 34. The crude phenol product, stream 35, is fed to the Phenol Finishing Tower 116, where product specification phenol is recovered overhead as stream 36. The AMS and cumene streams 30 and 34 are fed to the AMS Recovery Tower 117 where AMS is recovered as product stream 39, while cumene as stream 38 is returned to the oxidizer reactor 101.

By controlling the split ratios $\alpha$ and $\beta$, the amount of AMS produced in the plant can be continuously set, from about zero to about 50 wt.% of the stream containing CHP; preferably from about zero to about 30 wt.% of the stream containing CHP; more preferably from about zero to about 20 wt.% of the stream containing CHP; and most preferably from about zero to about 15 wt.% of the stream containing CHP, to meet the demand of the market for AMS.

Figure 2:
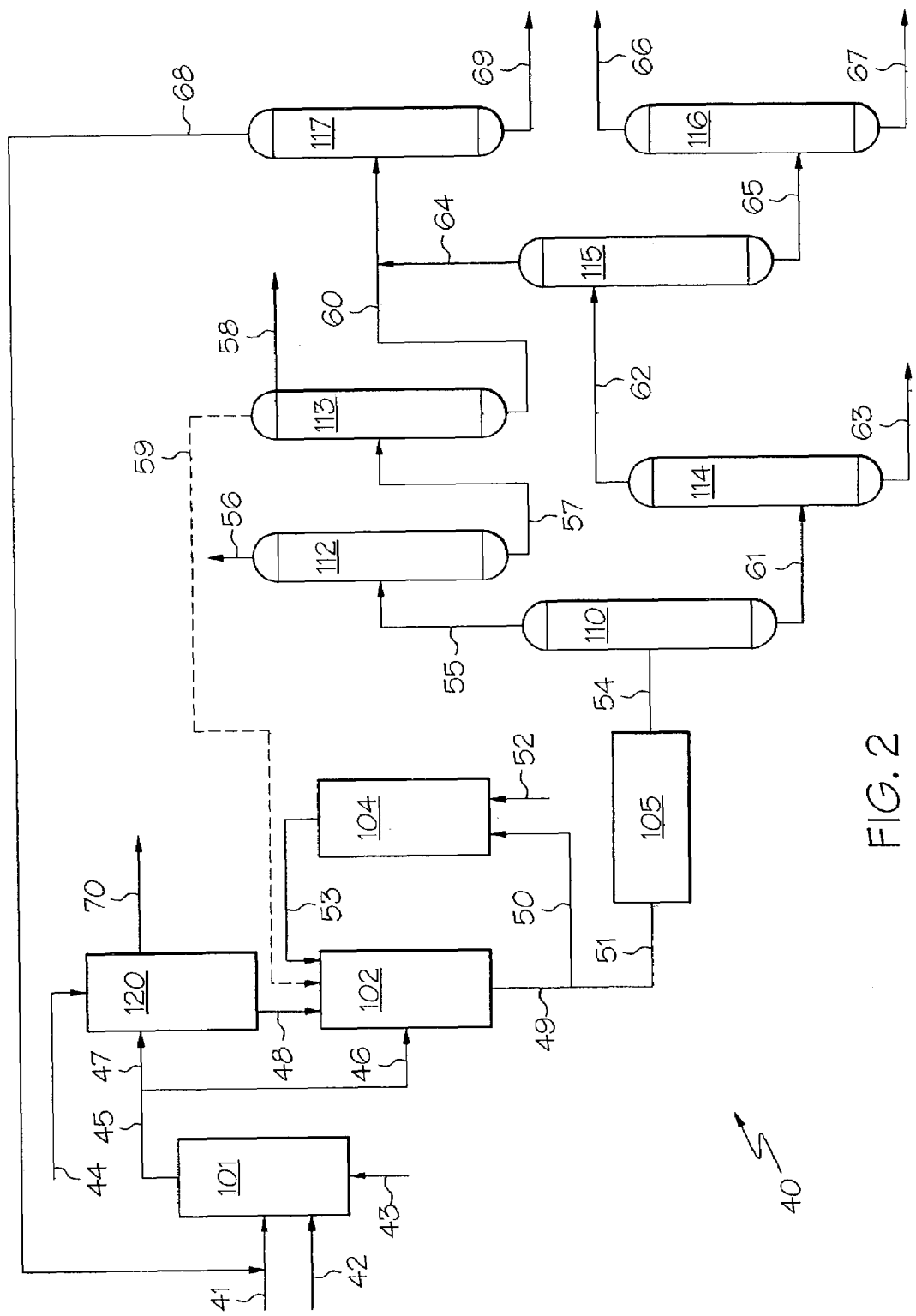
FIG. 2 is a schematic flow diagram of a processing scheme for the co-production of phenol, acetone, AMS, and propylene oxide.

FIG. 2 represents a schematic flow diagram of still another embodiment of this invention as processing scheme 40 for the co-production of propylene oxide, AMS, phenol, and acetone. Cumene in stream 41 is fed to an oxidation reactor 101 where CHP is produced by reaction of the cumene with oxygen from the air fed as stream 42. Initiators to facilitate the oxidation of the cumene may be added as stream 43. Preferably, these initiators may be an organic hydroperoxide such as CHP, tert-butyl hydroperoxide, ethylbenzene hydroperoxide or the like. Alternatively, these initiators may be free radical initiators known to catalyze the oxidation of organic hydrocarbons such as the azo type free radical initiators or any of the peroxy type free radical initiators or the like, as disclosed above with respect to processing scheme 1. The CHP stream 45, containing DMPC and acetophenone, together with unreacted cumene may be concentrated by removing a portion of the unreacted cumene prior to the cleavage section of the processing scheme 40.

The CHP stream 45 is then split into streams 46 and 47, with the split ratio α=47/46 set according to desired plant output of AMS. Stream 47 is fed to the epoxidation reactor 120 where a portion of the CHP in stream 47 reacts with a propylene-containing feed stream 44 to produce propylene oxide as a product stream 70. During the epoxidation reaction, CHP is reduced to DMPC over a suitable epoxidation catalyst, which include titanium supported on silica or molybdenum. Preferably, such epoxidation catalysts may be the catalysts disclosed in U.S. Pat. No. 6,114,551, incorporated herein by reference. Stream 48 leaving the reduction reactor, therefore, has an increased concentration of DMPC relative to CHP stream 45. Streams 48 and 46 are fed to first cleavage reactor 102 where an acidic catalyst decomposes the CHP into phenol and acetone, and dehydrates the DMPC into AMS. Preferably, suitable acidic catalysts, such as a mixed metal oxide, are the same as those disclosed above with respect to processing scheme 1. The effluent from first cleavage reactor 102 is comprised mainly of phenol, acetone, AMS, acetophenone, cumene, and some heavies produced from secondary reactions.

To minimize the formation of heavies, it is preferable to dilute the AMS in the cleavage reactor. One possible diluting stream is the product itself. If first cleavage reactor 102 is operated with an acidic catalyst in a plug flow reactor configuration, it is desirable to have as low as possible an AMS concentration at the inlet to minimize secondary reactions of the AMS. To achieve this goal, it is desirable to minimize the AMS in the diluting stream 53. This may be achieved by hydrogenating a portion of the effluent stream 49 as stream 50. Stream 50 is hydrogenated in hydrogenation reactor 104, in the presence of hydrogen fed stream 52 and a hydrogenation catalyst (not shown).

Suitable catalysts for use in the hydrogenation reactor 104 include noble metals such as palladium and platinum supported on a support that may, or may not, be acidic as disclosed above. The diluting stream 53 may be fed completely into the front end of the hydrogentation reactor 104. Alternatively, the diluting stream 53 may be fed in one or more stages down the length of the bed to provide the necessary diluting effect. The split ratio β=50/51 is set to provide the necessary diluent to minimize the formation of heavy components. Increasing β reduces the amount of heavy components produced in the cleavage reactor(s), but does so at the cost of a loss of recoverable AMS. As an alternative diluent, or in addition to the product recycle, acetone from the acetone tower 113 may be returned to the cleavage reactor in stream 59.

Stream 51 from the first cleavage reactor 102 may be sent to a second cleavage reactor 105. Second cleavage reactor 105 may be operated at conditions that are the same or are different than those in first cleavage reactor 102. For example, second cleavage reactor 105 may be operated at a higher temperature than first cleavage reactor 102. Cleavage reactor 105 would typically be a plug-flow reactor, and may, or may not contain a catalyst bed. If a liquid acid such as sulfuric acid is used in reactor 102, there may be sufficient acidity remaining in stream 51 to catalyze the necessary reactions in reactor 105. In a preferred embodiment, cleavage reactor 105 contains a solid acid catalyst, such as those described in U.S. Pat. Nos. 6,169,215; 6,169,216; and 6,297,406. Cleavage reactor 105 is used to decompose any dicumyl peroxide that may form in first reactor 102, and convert any residual CHP to phenol and acetone. In an alternative embodiment, a series of two or more reactors may be used for final conversion of the CHP, and a diluent such as acetone may or may not be added before each reactor bed.

While it is preferable to use a solid catalyst in cleavage reactors 102 and 105 as discussed above, it is within the scope of this invention to utilize liquid acids such as sulfuric acid to accomplish the decomposition of the CHP. If use is made of liquid acids, a neutralization step would be required prior to the recovery section of the plant (not shown). Such a neutralization step may employ liquid bases or ion exchange resins or the like, as is well known to those skilled in the art.

There are many ways known to those skilled in the art to separate the individual components from stream 54 exiting the cleavage section of the plant. The following distillation scheme is presented for illustrative purposes only. Stream 54 from the cleavage reactor is sent to the Crude Acetone Tower 110 where acetone and the lighter components are separated from phenol and the heavier components. The overhead stream 55 is sent to the Lights Topping Tower 112 where light compounds such as acetaldehyde are removed as stream 56. The bottoms from the topping tower, stream 57 are fed to the Refined Acetone Column 113, where product specification acetone is recovered as stream 58. The bottoms from the Crude Acetone Tower 110, stream 61, comprising phenol, and some AMS, cumene, acetophenone and heavies, is fed to the Heavy Ends Tower 114, where the heavy components are separated as stream 63. The overhead stream 62 is fed to the Hydrocarbon Removal Tower 115, where the residual AMS and cumene are separated from the phenol and pass to the AMS recovery section as stream 64. The crude phenol product, stream 65, is fed to the Phenol Finishing Tower 116, where product specification phenol is recovered overhead as stream 66. The AMS/cumene streams 60 and 64 are fed to the AMS Recovery Tower 117 where AMS is recovered as product stream 69, while cumene as stream 68 is returned to the oxidizer reactor 101.

By controlling the split ratios α and β, the amount of AMS produced in the plant can be continuously set, from about zero to about 50 wt.% of the stream containing CHP; preferably from about zero to about 30 wt.% of the stream containing CHP; more preferably from about zero to about 20 wt.% of the stream containing CHP; and most preferably from about zero to about 15 wt.% of the stream containing CHP to meet the demand of the market for AMS. In addition, propylene oxide, a high-valued product, is produced.

The invention will now be more particularly described with reference to the following Examples. For processing scheme 1, a suitable heterogeneous catalyst is required for use in reactor 103. Examples 1 and 3 will describe the synthesis of such a catalyst. Examples 2 and 4 will describe the use of these catalysts for reducing CHP to DMPC.

EXAMPLE 1

A solution containing 500 g of water, 45 g of concentrated phosphoric acid, 117 g of cobalt nitrate and 75 g of concentrated sulfuric acid was prepared with mixing. Another solution was prepared containing 1600 g of water and 300 g of aluminum sulfate. These two solutions were combined with stirring. The molar ratio of the cobalt/aluminum/phosphorous was 1/8/1. The pH of the product was adjusted to 9 by the addition of a 50 wt.% solution of sulfuric acid. The material was placed in a polypropylene bottle and put in a steam box (100° C.) for 48 hours. The material was then filtered and washed and dried at ~85° C. A portion of the material was air calcined to 540° C. for six hours. The elemental analyses and physical properties were as shown in Table I.

TABLE I

| Element | wt. % |
|---|---|
| Co | 7.1 |
| Al | 25.3 |
| P | 3.4 |
| Surface Area, m$^2$/g | 145 |

A portion of the above material was treated with a 0.1N solution of ammonium nitrate (100 ml of 0.1N ammonium nitrate solution to 10 g of calcined material). This treatment was done a total of four times with fresh solution. The material was then filtered, washed and dried at ~85° C. A portion of the material was air calcined to 540° C. for six hours. The surface area of this material was 310 m2/g.

EXAMPLE 2

To a 250-ml round bottom flask fitted with a condenser, stirrer and dropping funnel, and located in a water bath for temperature control, was charged a mixture of 100.0 g of acetone and 1.00 g of the catalyst of Example 1. The mixture was heated to reflux (57° C.) with stirring, and 50.0 g of 80 wt.% CHP solution (analyzed as 80.8 wt.% CHP, 7.7 wt.% cumene, 6.9 wt.% DMPC, 2.1 wt.% acetophenone) was added dropwise at an approximate rate of 2 g/min. Following addition of the CHP solution, small samples (~0.2 ml) of the reactant solution were withdrawn at regular intervals, filtered, and analyzed by gas chromatograph (GC).

Table II below shows the composition (wt.%) of the reactant solution at 1 and 3 hours after the addition of the CHP was complete. For analyzing the data in Table II, the following definitions are provided:

CHP Conversion (%)=(wt.% CHP$_{feed}$-wt.% CHP$_{product}$)/(wt.% CHP$_{feed}$)

% Increase in DMPC=(wt.% DMPC$_{product}$-wt.% DMPC$_{feed}$)/(wt.% DMPC$_{feed}$)

TABLE II

|  | Feed | 1 hr | 3 hr |
|---|---|---|---|
| Acetone | 66.67 | 66.97 | 66.72 |
| Cumene | 2.56 | 2.41 | 2.31 |
| Phenol | 0.09 | 0.05 | 0.06 |
| α-Methyl Styrene | 0.07 | 0.15 | 0.16 |
| Acetophenone | 0.70 | 1.57 | 1.97 |
| DMPC | 2.36 | 5.95 | 7.67 |
| Cumene Hydroperoxide | 26.93 | 22.53 | 20.71 |
| CHP Conversion |  | 16.4% | 23.1% |
| % Increase in DMPC |  | 152.4% | 225.2% |

The above example shows that the Co/Al/PO$_4$ catalyst reduces the CHP to DMPC. The catalyst, being non-acidic, is inactive for the decomposition of CHP into phenol and acetone.

EXAMPLE 3

Two hundred and fifty grams of ZrOCl$_2$.8H$_2$O and 88 g of Co(NO$_3$)$_2$.6H$_2$O were dissolved with stirring in 1.5 liters of distilled water. Another solution containing 130 g of conc. NH$_4$OH and 1.6 liters of distilled water was prepared. These two solutions were combined at the rate of 50 ml/min using a nozzle mixing. The pH of the final composite was adjusted to approximately 9 by the addition of concentrated ammonium hydroxide. This slurry was then put in polypropylene bottles and placed in a steambox (100° C.) for 72 hours. The product formed was recovered by filtration, washed with excess water, and dried overnight at 85° C. A portion of this catalyst was calcined to 800° C. in flowing air for 3 hours to form a catalyst having 20% Co, by weight.

EXAMPLE 4

To a 250-ml round bottom flask fitted with a condenser, stirrer and dropping funnel, and located in a water bath for temperature control, was charged a mixture of 100.0 g of acetone and 1.00 g of the catalyst of Example 3. The mixture was heated to reflux (57° C.) with stirring, and 50.0 g of 80 wt.% CHP solution (analyzed as 80.8 wt.% CHP, 7.7 wt.% cumene, 6.9 wt.% DMPC, 2.1 wt.% acetophenone) was added dropwise at an approximate rate of 2 g/min. Following addition of the CHP solution, small samples (~0.2 ml) of the reactant solution were withdrawn at regular intervals, filtered, and analyzed by GC.

Table III below shows the composition (wt.%) of the reactant solution at 1 and 3 hours after the addition of the CHP was complete.

TABLE III

|  | Feed | 1 hr | 3 hr |
|---|---|---|---|
| Acetone | 66.67 | 67.37 | 67.32 |
| Cumene | 2.56 | 2.27 | 2.20 |
| Phenol | 0.09 | 0.04 | 0.03 |
| α-Methyl Styrene | 0.07 | 0.13 | 0.13 |
| Acetophenone | 0.70 | 2.29 | 2.43 |
| DMPC | 2.36 | 8.52 | 9.95 |
| Cumene Hydroperoxide | 26.93 | 19.17 | 17.48 |
| CHP Conversion |  | 28.8% | 35.1% |
| % Increase in DMPC |  | 261.2% | 321.9% |

The above example shows that a Co/ZrO$_2$ catalyst reduces the CHP to DMPC. The catalyst, being non-acidic, is inactive for the decomposition of CHP into phenol and acetone.

EXAMPLE 5

The catalysts of Examples 1 and 3 are suitable for use in reactor 103 of processing scheme 1. By adjusting the split ratio α, and using the processing parameters of temperature and contact time to control the conversion, varying percentages of the CHP stream 14 can be reduced to DMPC. For illustrative purposes, a material balance for processing scheme 1 is shown in Table IV where the amount of CHP reduced is varied between 0 and about 12%, by weight.

TABLE IV

| % CHP Reduced | 0 | 5 | 7 | 11.8 |
|---|---|---|---|---|
| Phenol Yield (%) | 94.1 | 88.9 | 86.8 | 81.8 |
| AMS Yield (%) | 80 | 171.6 | 208.2 | 296.1 |
| AMS/Phenol (%) | 3.5 | 8 | 10 | 15 |

The phenol yield shown in Table IV is the amount of phenol produced as a percentage of the cumene fed to 101 that is converted. The AMS yield shown in Table IV is the amount of AMS produced in the plant relative to the amount of DMPC produced in the oxidation step. As is shown in Table IV, by varying the amount of CHP reduced from zero to about 12%, the ratio of AMS to phenol produced in the plant can be varied from 3.5% to about 15%.

As is known by those skilled in the art, there are many factors that influence the yields of a phenol plant. There are many processing steps in the production of phenol, as illustrated in processing schemes 1 and 40, that influence the overall production yields. For illustrative purposes of this example, the following selectivities have been postulated. In the oxidation step, the selectivity of cumene to CHP in reactor 101 is about 95%. The selectivity to DMPC for the non-CHP oxidized products is about 83%. The selectivity in first cleavage reactor 102 and second cleavage reactor 105, to phenol and acetone is about 99.5%. The selectivity to AMS in the dehydration reaction is about 80%. The remaining 20 percent of the AMS is converted to AMS dimers and p-cumylphenol.

As shown in Table IV, the phenol and AMS yields are a function of the CHP that is reduced in the reduction reactor 103. A reduction of about 7% of the CHP produced in the oxidation reactor 101 represents an AMS yield relative to the amount of phenol produced by the plant of about 10%, representing a yield in excess of 200% which is more than double that produced without the use of a reduction reactor.

The additional DMPC that is produced is independent of the method by which the CHP is reduced. Consequently, the AMS yields are the same irrespective of whether the DMPC is formed via a reduction reaction as in the scheme of FIG. 1 or in an epoxidation reaction as shown in the scheme of FIG. 2.

We claim:

1. A process for producing α-methylstyrene, acetone and phenol comprising the steps of:
    (a) oxidizing cumene in the presence of oxygen to form cumene hydroperoxide;
    (b) selectively reducing a portion of said cumene hydroperoxide formed in step (a) in the presence of a non-acidic catalyst to form dimethyl phenyl carbinol; and
    (c) contacting a remaining portion of said cumene hydroperoxide and said dimethyl phenyl carbinol in the presence of an acidic catalyst to form α-methylstyrene, acetone and phenol.

2. The process of claim 1, wherein said non-acidic catalyst of step (b) is comprised of a metal and a first catalyst support, said metal is selected from the group consisting of Group 1 metal, a Group 2 metal, a Group 3 metal, a Group 8 transition metal, a Group 9 transition metal, a Group 10 transition metal, and mixtures thereof.

3. The process of claim 2, wherein said first catalyst support is selected from the group consisting of silica, alumina, crystalline or amorphous aluminophosphates, Group 4 metal oxides, mesoporous molecular sieves, and mixtures thereof.

4. The process of claim 3, wherein said metal is cobalt and said first catalyst support is zirconium oxide.

5. The process of claim 3, wherein said metal is cobalt and said first catalyst support is aluminophosphate.

6. The process of claim 1, wherein said acidic catalyst of step (c) is selected from the group consisting of a liquid catalyst and a solid acid catalyst.

7. The process of claim 6, wherein said liquid catalyst is sulfuric acid.

8. The process of claim 6, wherein said solid acid catalyst is selected from the group consisting of a Group 4 metal oxide that has been modified by a Group 6 metal oxide, a sulfated transition metal oxide, a mixed metal oxide of cerium oxide and a Group 4 metal oxide, and mixtures thereof.

9. The process of claim 1, wherein step (c) further includes contacting a diluent stream with said remaining portion of said cumene hydroperoxide and said dimethyl phenyl carbinol in the presence of said acidic catalyst to form α-methylstyrene, acetone and phenol.

10. The process of claim 9, wherein said diluent stream is acetone.

11. The process of claim 9, further comprising the step of:
    (d) contacting a portion of said α-methylstyrene formed in step (c) with hydrogen in the presence of a hydrogenation catalyst to form said diluent stream of step (c).

12. The process of claim 11, wherein said hydrogenation catalyst comprises a hydrogenation component and a second catalyst support.

13. The process of claim 12, wherein said hydrogenation component is selected from the group consisting of a Group 6 metal, a Group 7 metal, a Group 8 metal, a Group 9 metal, a Group 10 metal, a Group 11 metal, and mixtures thereof.

14. The process of claim 13, wherein said Group 10 metal is palladium or platinum.

15. The process of claim 12, wherein said second catalyst support is selected from the group consisting of alumina, silica, clay, carbon, zirconia, titania, mesoporous molecular sieves, and mixtures thereof.

16. The process of claim 1, wherein said portion of said cumene hydroperoxide that is reduced in reducing step (b) comprises from about zero to 50 weight percent of said cumene hydroperoxide in step (a).

17. The process of claim 16, wherein said portion of said cumene hydroperoxide that is reduced in reducing step (b) comprises from about zero to 15 weight percent of said cumene hydroperoxide in step (a).

18. The process of claim 1, wherein said oxidizing step (a) includes oxidizing said cumene in the presence of an initiator.

19. The process of claim 18, wherein said initiator is selected from the group consisting of cumene hydroperoxide, tert-butyl hydroperoxide, ethylbenzene hydroperoxide, azo type free radical initiators, peroxy type free radical initiators, and mixtures thereof.

20. The process of claim 1, further comprising the step of:
    (d) reacting said remaining portion of said cumene hydroperoxide and any dicumyl peroxide formed in step (c) with a second acidic catalyst to form phenol, acetone, and α-methylstyrene.

21. The process of claim 20, wherein said second acidic catalyst is a solid acid catalyst or a liquid acid catalyst.

22. A process for producing phenol, acetone and α-methylstyrene, comprising the steps of:
    (a) oxidizing a cumene stream in an oxidation reactor in the presence of an oxygen stream, to form a oxidized stream which comprises cumene hydroperoxide and dimethyl phenol carbinol;
    (b) supplying a selected portion of said oxidized stream to a reduction reactor having an non-acidic catalyst, to form a reduced stream which comprises dimethyl phenyl carbinol; and
    (c) supplying said reduced stream and a remaining portion of said oxidized stream to a cleavage reactor having an acidic catalyst, to form an effluent stream which comprises phenol, acetone and α-methylstyrene.

23. The process of claim 22, wherein said selected portion of said oxidized stream is in an amount sufficient to produce an α-methylstyrene to phenol ratio in said effluent stream of about 3.5 percent or greater.

24. The process of claim 22, wherein said ratio of α-methylstyrene to phenol is between about 3.5 percent to 15 percent.

25. The process of claim 22, wherein essentially none of said oxidized stream of step (a) is supplied to said reduction reactor.

26. The process of claim 22, wherein said acidic catalyst is a liquid acid catalyst or a solid acid catalyst.

27. The process of claim 26, wherein said liquid acid catalyst is sulfuric acid.

28. The process of claim 26, wherein said solid acid catalyst is selected from the group consisting of a Group 4 metal oxide that has been modified by a Group 6 metal oxide, a sulfated transition metal oxide, a mixed metal oxide of cerium oxide and a Group 4 metal oxide, and mixtures thereof.

29. The process of claim 22, wherein said hydrogenation catalyst comprises a hydrogenation component and a catalyst support.

30. The process of claim 29, wherein said hydrogenation component is selected from the group consisting of a Group 6 metal, a Group 7 metal, a Group 8 metal, a Group 9 metal, a Group 10 metal, a Group 11 metal, and mixtures thereof.

31. The process of claim 30, wherein said Group 9 metal is palladium or platinum.

32. The process of claim 29, wherein said catalyst support is selected from the group consisting of alumina, silica, clay, carbon, zirconia, titania, mesoporous molecular sieves, and mixtures thereof.

33. A process for producing phenol, acetone and α-methylstyrene, comprising the steps of:
(a) oxidizing a cumene stream in an oxidation reactor in the presence of an oxygen stream, to form a oxidized stream which comprises cumene hydroperoxide and dimethyl phenol carbinol;
(b) supplying a portion of said oxidized stream to a reduction reactor having an non- acidic catalyst, to form a reduced stream which comprises dimethyl phenyl carbinol;
(c) supplying said reduced stream and a remaining portion of said oxidized stream to a first cleavage reactor having a first acidic catalyst, to form a first effluent stream which comprises phenol, acetone and α-methylstyrene; and
(d) hydrogenating a selected portion of said first effluent stream in a hydrogenation reactor having a hydrogenation catalyst in the presence of a hydrogen stream, to form a diluent stream that is recycled to said first cleavage reactor;
(e) supplying a remaining portion of said first effluent stream to a second cleavage reactor having a second acidic catalyst to form a second effluent stream comprising additional amounts of phenol, acetone and α-methylstyrene than said first effluent stream;
(f) separating said second effluent stream in a separation zone to form a phenol stream, an acetone stream, and an α-methylstyrene stream; and
wherein said selected portion of said first effluent stream that is hydrogenated to form said diluent stream is in an amount effective to minimize the formation of components heavier than α-methylstyrene in said first cleavage reactor.

34. The process of claim 33, wherein step (c) includes supplying said diluent stream which comprises acetone.

35. The process of claim 33, wherein said ratio of α-methylstyrene to phenol in said second effluent stream is about 3.5 percent or greater.

36. The process of claim 33, wherein said first acidic catalyst or said second acidic catalyst is a liquid acid catalyst or a solid acid catalyst.

37. The process of claim 36, wherein said liquid acid catalyst is sulfuric acid.

38. The process of claim 36, wherein said solid acid catalyst is selected from the group consisting of a Group 4 metal oxide that has been modified by a Group 6 metal oxide, a sulfated transition metal oxide, a mixed metal oxide of cerium oxide and a Group 4 metal oxide, and mixtures thereof.

39. A method of using a non-acidic catalyst comprising the step of contacting said non-acidic catalyst with cumene hydroperoxide to form dimethyl phenyl carbinol, said non-acidic catalyst comprised of a transition metal selected from the group consisting of a Group 8, Group 9 and Group 10, and a catalyst support.

* * * * *